United States Patent
Casanova Yepes et al.

(10) Patent No.: US 12,409,429 B2
(45) Date of Patent: Sep. 9, 2025

(54) METHOD FOR COATING INSOLUBLE SOLIDS

(71) Applicants: Suministros de Colombia S.A.S., Sabaneta (CO); UNIVERSIDAD DE ANTIOQUIA, Medellín (CO)

(72) Inventors: Herley Casanova Yepes, Barranquilla (CO); Felipe Delgado Ospina, Barranquilla (CO); Jorge Osvaldo Jaimes Jaimes, Barranquilla (CO); Julián Andrés Sánchez Rendón, Barranquilla (CO); Juan Diego Torres Oquendo, Medellín (CO)

(73) Assignees: Universidad de Antioquia, Medellin (CO); Suministros de Colombia S.A.S., Sabaneta (CO)

( * ) Notice: Subject to any disclaimer, the term of this patent is extended or adjusted under 35 U.S.C. 154(b) by 712 days.

(21) Appl. No.: 17/440,061

(22) PCT Filed: Mar. 17, 2020

(86) PCT No.: PCT/IB2020/052433
§ 371 (c)(1),
(2) Date: Jan. 17, 2022

(87) PCT Pub. No.: WO2020/188483
PCT Pub. Date: Sep. 24, 2020

(65) Prior Publication Data
US 2022/0161218 A1    May 26, 2022

(30) Foreign Application Priority Data
Mar. 18, 2019  (CO) ................... NC2019/0002535

(51) Int. Cl.
*B01J 13/04* (2006.01)
*A61K 9/50* (2006.01)
*B01J 13/20* (2006.01)

(52) U.S. Cl.
CPC ........... *B01J 13/046* (2013.01); *A61K 9/5036* (2013.01); *A61K 9/5052* (2013.01); *B01J 13/20* (2013.01)

(58) Field of Classification Search
CPC ....... B01J 13/046; B01J 12/20; A61K 9/5036; A61K 9/5052
See application file for complete search history.

(56) References Cited

FOREIGN PATENT DOCUMENTS

| | | |
|---|---|---|
| CO | 06073148 A | 7/2006 |
| CO | 5720213 A1 | 1/2007 |
| WO | 2015028920 A1 | 3/2015 |

OTHER PUBLICATIONS

Aude Met. al. Encapsulation of Natural Polyphenolic Compounds; a Review. Pharmaceutics 3(2011), 793-829.
Miladi K. et al. Drug carriers in Osteoporosis: Preparation, drug encapsulation and applications. International Journal of Pharmaceutics445 (2013), 181-195.
Anil, K. Ionotropic cross-linked chitosan microspheres for controlled release of ampicillin. Int. Journal of Pharmaceutics 312 (2006), 166-173.
Delgado, F. (2017). Use of a Protein as Functionalizing Agent to Produce Low Apparent Density Kaolin. In XVI International Clay Conference (vol. 7, pp. 1-10). Granada, Spain; Digilabs.
Delgado, F., Jaimes, J., Sanchez, J., & Casanova, H. (Apr. 2018). Milk Protein Functionalized Mineral Particles as a Technological Platform for the Food Industry. Medellín, Colombia; Universidad de Antioquia (UdeA).
Jaimes, J., Torres, J. D., & Casanova, H. (Apr. 2018). Improving Ice Cream Melting Resistance by Using Milk Protein Functionalized Calcium Carbonate. Medellín, Colombia; Universidad de Antioquia (UdeA).
Annan N. et al. Encapsulation in alginate-coted gelatin microspheres improves survival of the probiotic Bifidobacterium adolescentis 15703T during exposure to simulated gastro-intestinal conditions. Food Research International 41 (2008), 184-193.
Huiyi S. Microencapsulated probiotics using emulsification technique coupled with internal or external gelation process. Carbohydrate Polymers 96 (2013), 181-189.
Sánchez, J., Torres J., & Casanova, H. (Jun. 2017). Adsorption and emulsification properties of tricalcium phosphate particles functionalized by milk proteins. Medellín, Colombia; Universidad de Antioquia (UdeA).
Jaimes, J., Villa, A., & Casanova, H. (Jun. 2017). Calcium carbonate-milk protein microcapsules for calcium controlled release under stomach acidic conditions to reduce calcium intake side effects. Medellín, Colombia; Universidad de Antioquia (UdeA).
Vasisht N., Factors and Mechanisms in Microencapsulation, Chapter 2. In: Factors and Microencapsulation in the Food Industry, 2014, Elsevier Inc.
Chen J., et al., Zein-based Core-Shell Microcapsules for Potential Delivery of Algae Oil and Lipophilic Compounds. Food & Function, 2019, 1504-1512 (10).

*Primary Examiner* — Shirley V Gembeh
(74) *Attorney, Agent, or Firm* — The Morales Law Firm; Joseph L. Morales, Esq.

(57) ABSTRACT

The invention relates to a process for coating water-insoluble solids by ionic gelation employing negatively-charged macromolecules and a source of polyvalent cations as film-forming materials, wherein the coating material represents not more than 10% (w/w) with regard to the total weight of the coated solid. The coated insoluble solids may be subsequently dried to generate surface-modified dry particles for use as active ingredients and/or excipients in the manufacture of pharmaceutical compositions or food products.

8 Claims, 11 Drawing Sheets

METHOD FOR COATING INSOLUBLE SOLIDS

FIELD OF THE INVENTION

This invention is related to the chemistry field, specifically to processes for coating insoluble solids, more specifically, processes for functionalizing water-insoluble solids by ionic gelation.

DESCRIPTION OF THE PRIOR ART

Microencapsulation processes of insoluble solids such as ionic gelation, acid precipitation, coacervation and layer-by-layer processes usually employ methods based on ionic interactions. Microencapsulation by ionic gelation consists of the extrusion or emulsification of an ionically charged macromolecule in the form of droplets, in a solution of a counterion, generating in its contact the immediate gelation of the droplet external part. Subsequently, the counterions persist in their diffusion towards the interior of the particle inducing its total gelation.

The ionic gelation method has been used for the microencapsulation of polyphenols (Aude M et al. Encapsulation of Natural Polyphenolic Compounds; a Review. Pharmaceutics 3 (2011), 793-829), osteoporosis drugs (Miladia K et al. Drug carriers in osteoporosis: Preparation, drug encapsulation and applications. International Journal of Pharmaceutics 445 (2013), 181-195), probiotics (Annan N et al Encapsulation in alginate-coated gelatin microspheres improves survival of the probiotic *Bifidobacterium adolescentis* 15703T during exposure to simulated gastro-intestinal conditions. Food Research International 41 (2008), 184-193, Huiyi S. Microencapsulated probiotics using emulsification technique coupled with internal or external gelation process. Carbohydrate Polymers 96 (2013), 181-189), antibiotics (Anil, K Ionotropic cross-linked chitosan microspheres for controlled release of ampicillin. Int. Journal of Pharmaceutics 312 (2006), 166-173.5) and for the generation of biocompatible capsules of active compounds.

A process for coating insoluble solids by ionic gelation is found, for example, in WO2015/028920 which comprises forming a matrix of charged macromolecules on the surface of water insoluble solids to generate microspheres by controlled adsorption of the macromolecules onto the solid surface. The process is carried out in the presence of polyvalent ions at low temperature and gelation occurs with increasing temperature of the system.

In the foregoing procedure, the final concentration of the matrix-forming material (i.e., macromolecules) is more than 10% of the complete microcapsule total mass. At these high concentrations of macromolecules, individual microcapsules or microcapsule agglomerates may be generated. Single dry microcapsules with sizes below 2 μm may be of interest for applications where suspensions with slow settling processes are required. However, the handling of these dry single microcapsules may cause health problems for personnel in contact with them. Therefore, the use of dry particle agglomerates with sizes larger than 10 μm, which are obtained in WO2015/028920, is preferred. However, these particle agglomerates maintain their agglomerate identity even after redispersion in water, which induces their complete sedimentation after several minutes, limiting their applications to systems requiring slow sedimentation processes.

Additionally, concentrations of macromolecules equal to or higher than 10% produce a thick shell on the solid particles, thereby generating core-shell type microcapsules. The microcapsule thick shell, greater than 10 nm, according to the transmission electron micrograph presented in WO2015/028920, insulates the core from interaction with external agents. However, high stability towards external agents may be a limitation for applications where a faster but controlled release of the microcapsule core components is required.

Similarly, the thick shell generated by the macromolecules on the solid particle should modify the surface chemistry of the microencapsulated particles. However, WO2015/028920 does not explain possible effects of the macromolecules on the surface chemistry of the microcapsules. Therefore, changes in the thickness of the microcapsule shell, due to modifications in the concentration of macromolecules in the system, may generate changes in the surface chemistry of the solid particles and diversify the applications of these surface-modified solid particles.

By means of the process disclosed below, it is achieved to generate systems with a thin coating, i.e., with a lower concentration of macromolecules, specifically macromolecule-coated or functionalized particles are generated by ionic gelation, where agglomerates of particles may be destroyed by dispersing them in a protic solvent, their surface chemistry may be adjusted depending on the concentration and composition of the macromolecules, and crystallization processes of the macromolecules are induced on the surface of the insoluble solid particles.

BRIEF DESCRIPTION OF THE INVENTION

By means of an ionic gelation process this invention makes it possible to coat or functionalize water-insoluble solids using charged macromolecules as functionalizing or coating compounds, wherein the concentration of macromolecules in the functionalized solid particle is less than 10%.

DETAILED DESCRIPTION

The invention relates to a process for functionalizing or coating water-insoluble solids, using charged macromolecules as functionalizing compounds on the surface of the insoluble solid particles, where the macromolecules may also present crystallization processes induced by the crystalline structure of the coated insoluble solid. The coating of the insoluble solid particles is achieved by ionic gelation induced by the addition of polyvalent cations to the suspension of insoluble solids, prior to the sub-ambient thermal treatment that allows a controlled gelation of the charged macromolecules.

Figure 1:
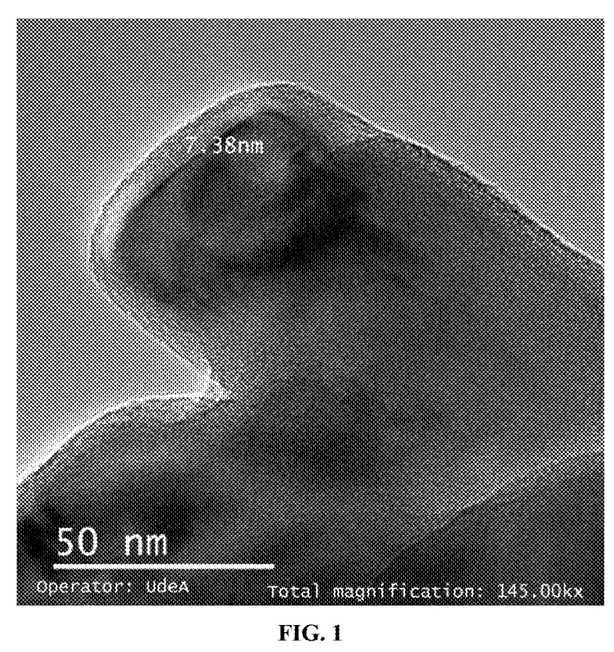
FIG. 1. Transmission electron micrograph of calcium carbonate coated with 2% sodium caseinate.

The coating process of this invention requires a concentration of macromolecules on the solid particle of less than 10% and may incorporate other additives, obtaining insoluble solids coated with a thin film (with a thickness of less than 10 nm according to the image obtained by transmission electron microscopy, FIG. 1) formed by one or more different macromolecules. This allows other functions to be given to the particles such as changes in surface chemistry (contact angle), capacity for redispersion and destruction of particle agglomerates, higher release rate of the compounds that form the solid particle subjected to external factors, and induction of crystallization processes of the macromolecules that coat the insoluble solid particles, where the system is formed by mineral particles, macromolecules and water. In particular, the contact angle obtained in the coated insoluble solids of this invention is lower than that of microcapsules with a protein content equal to or greater than 10% (Example 6).

The addition of a negatively charged macromolecule to an aqueous suspension of the insoluble solid, followed by heat treatment and the addition of polyvalent cations, induces the adsorption of these compounds on the surface of the insoluble solid particles and leads to the solid coating, forming a stable suspension of coated solids.

The concentration of the charged macromolecules and of the polyvalent cations used in the process, as well as the pH and the drying conditions, result in the size and morphology of the particles, which may be spheroidal or amorphous, with diameters ranging from 0.1 to 2000 micrometers. The process of coating water-insoluble solids of this invention allows retention of more than 80% of the functionalizing material on the surface of the coated solid obtained, which generates a greater efficiency to the process, where less than 20% of the coating material remains in solution after the process.

Thus, the process of coating water-insoluble solids of this invention, comprises preparing an aqueous suspension of water-insoluble solids and preparing a solution of negatively charged macromolecules; mixing the solution of negatively charged macromolecules with the suspension of water-insoluble solids by applying agitation and under sub-ambient temperature or sub-temperature until a mixture or second suspension is obtained. Finally, a source of polyvalent cations is added to the second suspension, until the coating of the insoluble solid is formed, wherein the content of macromolecules in the coating is less than 10% with regard to the total weight of the coated solid.

Water-insoluble solids generate surface charge when suspended in water or in another protic solvent, as a result of the dissociation of their functional groups when interacting with the solvent.

Insoluble solids are metallic or non-metallic minerals among which are iron oxides, calcium oxides, magnesium oxides, zinc oxides, calcium phosphate salts, insoluble calcium salts, aluminosilicates, polymeric particles, kaolin and insoluble solids obtained by synthesis, extraction or by bioprocesses or mixtures thereof. Additionally, other insoluble solids may be phyllosilicates (such as Antigorite—$Mg_3Si_2O_5(OH)_4$, Chrysotile—$Mg_3Si_2O_5(OH)_4$, Lizardite—$Mg_3Si_2O_5(OH)_4$, Kaolinite—$Al_2Si_2O_5(OH)_4$, Illite—$(K, H_3O)(Al, Mg, Fe)_2(Si, Al)_4O_{10}[(OH)_2, (H_2O)]$, Smectite, Montmorillonite—$(Na, Ca)_{0.33}(Al, Mg)_2(Si_4O_{10})(OH)_2 \cdot nH_2O$, Vermiculite—$(MgFe, Al)_3(Al, Si)_4O_{10}(OH)_2 \cdot 4H_2O$, Talc—$Mg_3Si_4O_{10}(OH)_2$, Pyrophyllite—$Al_2Si_4O_{10}(OH)_2$, Biotite—$K(Mg, Fe)_3(AlSi_3O_{10})(OH)_2$, Muscovite—$KAl_2(AlSi_3O_{10})(OH)_2$, Phlogopite—$KMg_3 \; AlSi_3O_{10}(OH)_2$, Lepidolite—$K(Li, Al)_{2-3}(AlSi_3O_{10})(OH)_2$, Margarite $CaAl_2(Al_2Si_2O_{10})(OH)_2$, Glauconite—$(K, Na)(Al, Mg, Fe)_2(SiAl)_4O_{10}(OH)_2$, Chlorite—$(Mg, Fe)_3(Si, Al)_4O_{10}(OH)_2 \cdot (Mg, Fe)_3(OH)_6$), calcium carbonate ($CaCO_3$), calcium phosphates, calcium sulfate ($CaSO_4$) or mixtures thereof. Calcium phosphate salts include but are not limited to monocalcium phosphate monohydrate $Ca(H_2PO_4) \cdot H_2O$, anhydrous monocalcium phosphate $Ca(H_2PO_4)_2$, dicalcium phosphate dehydrate (brushite) $CaHPO_4 \cdot 2H_2O$, anhydrous dicalcium phosphate (monetite) $CaHPO_4$, octacalcium phosphate $Ca_8(HPO_4)_2(PO_4)_4 \cdot 5H_2O$, alpha-tricalcium phosphate $Ca_3(PO_4)_2$, tricalcium beta-phosphate $Ca_3(PO_4)_2$, amorphous calcium phosphate $Ca_x(PO_4)_y \cdot nH_2O$, hydroxyapatite $Ca_{10}(PO_4)_6 \cdot (OH)_2$ or mixtures thereof. The concentration of insoluble solids in the aqueous suspension is between 1% and 80%, between 1% and 70%, between 1 and 5%, between 1 and 10%, between 5 and 15%, between 10 and 20%, between 15 and 20%, between 25 and 40%, between 45 and 60%, between 70% and 80%, or between 90% and 99% (w/w).

In order to achieve a homogeneous coating process, it is necessary to keep the suspension of solids under permanent agitation to avoid sedimentation. It is suggested that the agitation should be at a minimum of 200 rpm, between 200 rpm and 500 rpm or between 200 rpm and 600 rpm, which are sufficient to avoid sedimentation of the particles. However, even higher agitation values may be required depending on the particle size of the suspension to be coated.

The particle diameter of the water-insoluble solid suitable to be coated according to the process of the invention is greater than 0.1 μm up to the order of millimeters, specifically from 50 nm upwards, or more specifically from 10 nm. In particular the primary particle size is less than 5 μm, is between 100 nm and 1 µm, or between 1 and 5 µm, or above 0.1 µm. The primary particles may be agglomerated to generate particles of size greater than 1 µm and up to 1000 µm. In the process of this invention the morphology, roughness or presence of pores of the water-insoluble solids does not represent a drawback for their coating, since the film formation is uniform along the extension of the solid surface.

The water insoluble solids are coated by macromolecules adsorbed on the particle surface. For this purpose, after preparing the suspension of water-insoluble solids, a solution of negatively-charged macromolecules is prepared.

Negatively-charged macromolecules are typically proteins, salts of proteins, polysaccharides or synthetic polymers or mixtures thereof. Proteins include milk proteins, gelatin, proteins from vegetal sources, albumins or mixtures thereof. Preferably, some proteins such as casein, sodium caseinate and calcium caseinate, whey, pea, soy proteins or mixtures thereof may also be employed. Negatively-charged polysaccharides comprise modified starches, gellan gum, gum arabic, xanthan, alginate salts, cellulose derivatives, pectin salts, carrageenans or mixtures thereof. Synthetic polymers include polyacrylates, polysulphates and polysulphonates or mixtures thereof. The macromolecules are negatively charged by adjusting the solution pH, which is corroborated by zeta potential measurements, obtaining values above 5 mV. The concentration of macromolecules in the solution is between 0.1 and 40%, between 0.1% and 20% w/w, between 30% and 70% w/w or between 40% and 60% w/w.

Optionally, a neutral, cationic and/or reducing sugar-type polysaccharide is added after addition of the polyvalent cation source to the mixture of the macromolecule solution, with the suspension of water-insoluble solids. In particular, uncharged polysaccharides such as guar gum, agar, maltodextrins and cyclodextrins may be employed subsequent to the ionic gelation process to provide additional functionalization. Positively charged polysaccharides such as chitosan may also be added to provide functionality to the particles obtained by ionic gelation.

Preferably, the macromolecule solution system has a sufficient hydration time, for example for 2 hours, between 1 and 5 hours, or between 1 and 8 hours or until the opening of the macromolecule structure occurs. This time depends on the macromolecule type. Optionally both the suspension of water-insoluble solids and the solution of negatively charged macromolecules are cooled, for example to 2° C. or 5° C.

The solution of negatively charged macromolecules is mixed with the suspension of insoluble solids in water with controlled agitation and temperature, generating surface charges on the insoluble solid. The agitation is between 200 rpm and 500 rpm, and the sub-temperature is below 15° C., below 10° C., below 8° C. or down to 2° C. Additionally, when mixing the suspension of water-insoluble solids with the solution of negatively-charged macromolecules, it is suggested to keep the temperature below 15° C., specifically below 10° C. or more specifically below 8° C.

The generation of surface charges on the water-insoluble solid may be verified by measuring the zeta potential, with absolute values usually above 5 mV to avoid flocculation or reversible flocculation. The system pH may be adjusted to modify the absolute value of the zeta potential, thus promoting the adsorption of charged film-forming macromolecules. In principle, the aim is to generate a pH where electrostatic attractions between the surface of the insoluble solid and the macromolecules are maximized without destabilizing the suspension, which may be monitored with the average particle size. The system pH depends on the protein and the solid, for example in the case of calcium carbonate, calcium sulfate and calcium phosphate, the pH should be above 5.5. However, systems such as kaolin are stable down to pH 1. In general, the pH may be modified until the system is stable or shows reversible flocculation.

In order to achieve an adequate hydration and interaction between the macromolecules and the surface of the water-insoluble solid, it is convenient to lower the temperature to sub-ambient values, preferably at temperatures below 10° C., below 8° C., or below 5° C., between 2 and 10° C., or at temperatures close to 5° C.

In order to induce the ionic gelation of the macromolecules on the surface of the insoluble solid, a source of polyvalent cations is added to the suspension mixture of insoluble solids and the negatively-charged macromolecules. The polyvalent cation source may be added directly to the system or preferably in solution with a concentration starting from 0.2 M and not exceeding 2 M, again, these values depend on the protein employed. Preferably, the source of polyvalent cations is added slowly to the mixture with stirring and sub-ambient temperature.

The source of polyvalent cations is a soluble salt or a slightly water-insoluble salt, e.g., a calcium salt, such as calcium chloride, calcium chloride dihydrate, calcium oxalate and calcium citrate. The addition of macromolecules and polyvalent cations at low temperature may be repeated several times to control the film thickness, controlling the concentration of each to avoid agglomeration of suspended particles. The source of polyvalent cations is in a concentration between 0.1% and 10%, between 0.05% and 3.0%, or between 0.5 and 5% (w/w), or between 4% and 7% (w/w).

The addition of the polyvalent cation source to the mixture produces an increase in the adsorption of the macromolecules on the surface of the insoluble solid.

In one embodiment, as part of the negatively charged macromolecules, a polysaccharide source such as maltodextrin is added at the end of the ionic gelation process (after carrying out the addition of a polyvalent cation source to the mixture). The polysaccharide source is between 1 and 40% (w/w), between 5 and 15% (w/w), between 8 and 12% (w/w), between 2 and 10% (w/w) in the suspension.

Subsequently, the mixture suspension of the macromolecule solution with the suspension of water insoluble solids and optionally the polysaccharide source, is dried at temperatures between 80 and 400° C., for example by means of a spray dryer, or any method known to a person skilled in the art.

Once the adsorption process is carried out, the system temperature is increased to induce its ionic gelation, which is achieved at temperatures close to 25° C. In some cases, the system temperature may be increased up to 80° C. By increasing the suspension temperature in the presence of polyvalent cations, the coating film of the insoluble solid is formed.

The ionic gelation process induces a high adsorption, higher than 80%, about 90% or even 99% of the macromolecules on the surface of the water-insoluble solid. Insoluble solids coated by macromolecules are obtained, without free particles or with free particles less than 20%, less than 10%, less than 5%, or between 5 and 20%.

Optionally, the process described above includes a drying step after obtaining the water insoluble solid coated with macromolecules, which involves an inlet temperature to the dryer above 180° C. and outlet temperatures above 80° C. For example, the suspension of coated insoluble solids may be dried by spray drying to generate surface-dried modified solids of insoluble solids. Depending on the drying conditions and the macromolecules employed, it is possible to generate individual coated solids or agglomerates of particles with geometric shapes ranging from spherical to amorphous agglomerates, which may be redispersible in water, maintaining their identity as agglomerates or may be individualized into their primary particles.

A water-insoluble solid coated with macromolecules is obtained, characterized in that it is coated with less than 10% of the total mass with macromolecules, where the water-insoluble solid is iron oxides, calcium oxides, magnesium oxides, zinc oxides, calcium phosphate salts, insoluble calcium salts, aluminosilicates, polymeric particles, kaolin and insoluble solids obtained via synthesis, extraction or by bioprocesses or mixtures thereof, wherein the coating is protein such as casein, sodium caseinate, calcium caseinate, whey proteins, pea, soybean, gum arabic, xanthan, alginate salts, cellulose derivatives, modified starches, gellan gum, pectin salts, carrageenans, polyacrylates, polysulphates and polysulphonates or mixtures thereof.

Coated water-insoluble solids or coated particles are obtained with a concentration of less than 10% of macromolecules, between 0.1% and 9.9% of macromolecules, between 4% and 9.9% of macromolecules, between 2% and 9.9% of macromolecules, or between 2 and 6% of macromolecules. The coated particles obtained are characterized by having a contact angle between 20 and 89°, between 70 and 89°, or between 60 and 70°. The particles must have a moisture content of less than 5%.

The coated water-insoluble solid obtained has a volume average size between 0.1 μm and 1000 μm, or between 4.0 μm and 500 μm. Obtaining agglomerates with a particle size around 1 μm, between 1 and 2000 μm, between 1 and 500 μm.

After drying, the coated water-insoluble solids may form particle aggregates, with a particle size between 1 and 2000 μm.

The insoluble coated solids and/or coated particles obtained by the process of this invention, may be used as active principles and/or as diluents, excipients or vehicles in the preparation of cosmetic, pharmaceutical and/or nutraceutical compositions requiring controlled release of compounds or in the preparation of foodstuffs. The insoluble coated solids or coated particles obtained by the process of this invention may be in amorphous or crystalline form depending on the heat treatment applied. The amorphous forms are more commonly used in foodstuffs, whereas the crystalline or ceramic forms are more commonly used in the area of implants, e.g., example in the manufacture of bone implants.

The coated insoluble solids and/or coated particles obtained by the process of this invention may induce crystallization of the macromolecules coating the insoluble solid. These induced crystallization processes may be employed in the manufacture of protein crystals for nutraceutical or pharmaceutical applications.

The use of the water-insoluble solids coated with macromolecules and the water-insoluble solids coated with macromolecules and polysaccharides, characterized above in the manufacture of frozen foods, specifically ice cream and/or frozen ice cream. In particular, a water insoluble solid coated with macromolecules obtained by means of the foregoing process may be incorporated in ice cream mixes, at concentrations between 0.1% and 10%, between 0.1% and 5%, or between 0.2% and 3%. Compared with other uncoated insoluble solids, this invention achieves coated insoluble solids, which provides higher viscosity to ice cream, without affecting the ice cream aeration process and, on the contrary, decreasing the aeration time by about 25%. Furthermore, the coated insoluble solid allows to control the melting of ice cream as a finished product.

The following Examples illustrate the invention, without the inventive concept being restricted thereto.

EXAMPLES

Example 1. Production of Protein-Coated Calcium Carbonate (98% $CaCO_3$, 2% Protein A solution of 200 g sodium caseinate (10% w/w) was prepared by hydration for at least 2 hours and cooling to 5° C. On the other hand, 2000 g of a calcium carbonate suspension (49% w/w) was prepared, which was then cooled to 5° C. and mixed with the sodium caseinate solution by stirring at 450 rpm. Once the mixing was finished, and keeping the temperature below 8° C., 200 g of a calcium chloride dihydrate solution (0.51% w/w) was slowly added to obtain the suspension of calcium carbonate particles with protein coating.

The suspension of protein-coated calcium carbonate was subsequently dried in a spray dryer in disc configuration at an inlet temperature of 320° C., outlet temperature of 90° C., ventilation rate of 150 $m^3$/h and feed pump speed of 50 mL/minute.

Figure 2:
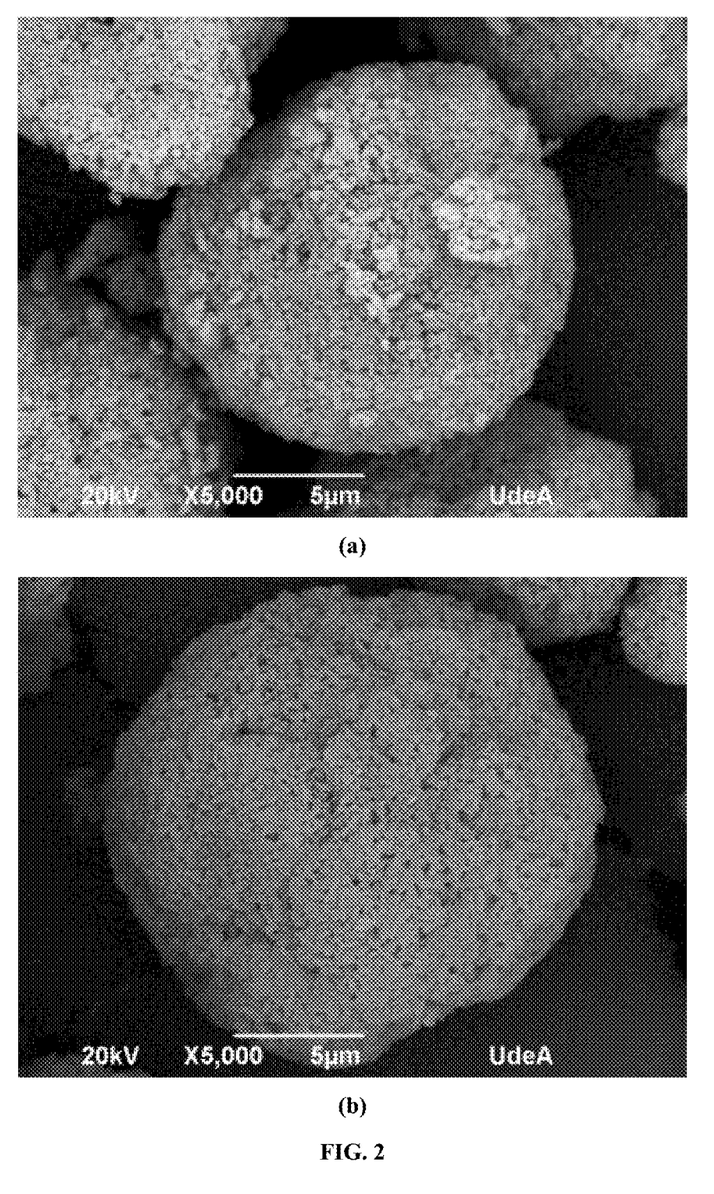
FIG. 2. Scanning electron micrographs of calcium carbonate with sodium caseinate: (a) 2% protein; (b) 10% protein (Example 1).

The contact angle measurement of the mineral coated with 2% protein, using the Washburn method in an automatic tensiometer K-12 (Krüss), generated a value close to 78°. Meanwhile, calcium carbonate microcapsules with a protein content equal to or higher than 10% presented contact angles close to 90°. The scanning electron micrographs (FIG. 2) present a comparison of the particle surfaces coated with 2% and 10% protein. For the 2% system, agglomerates of particles with a size close to 15 μm formed by primary particles of less than 1 μm in size, with an irregular surface and with the presence of free particles were observed. For the system with 10% protein, the particle agglomerates were close to 15 μm in size and presented a homogeneous surface, without the presence of free particles.

The measurement of free protein by ultraviolet-visible spectrophotometry indicated a value lower than 10% for calcium carbonate 98% $CaCO_3$ and 2% protein, while the values obtained for calcium carbonate 90% $CaCO_3$ and 10% protein, presented free protein values between 10 and 20%.

Figure 3:
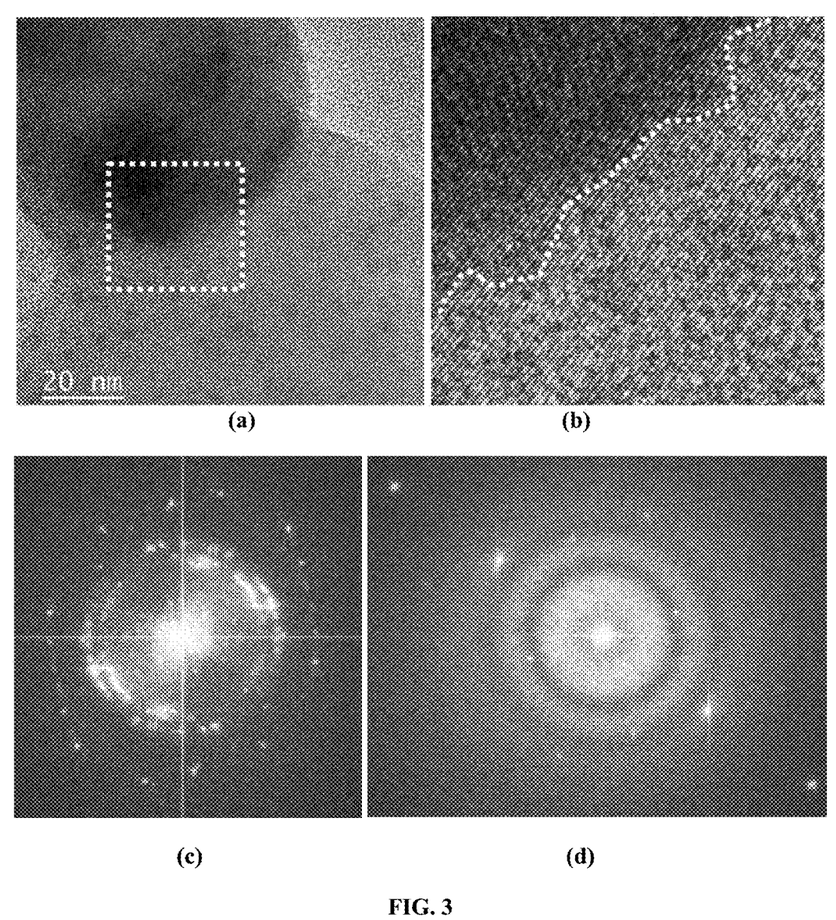
FIG. 3. Crystallinity degree analysis of calcium carbonate particles coated with 2% sodium caseinate: (a) Transmission electron microscopy 195000×; (b) Close-up on bounded area in FIG. 3a, the dotted line indicates the boundary between protein (bottom) and calcium carbonate (top); (c) Diffraction patterns of the mineral on bounded area in FIG. 3b; (d) Diffraction patterns of the protein coating on bounded area in FIG. 3b.
Figure 4:
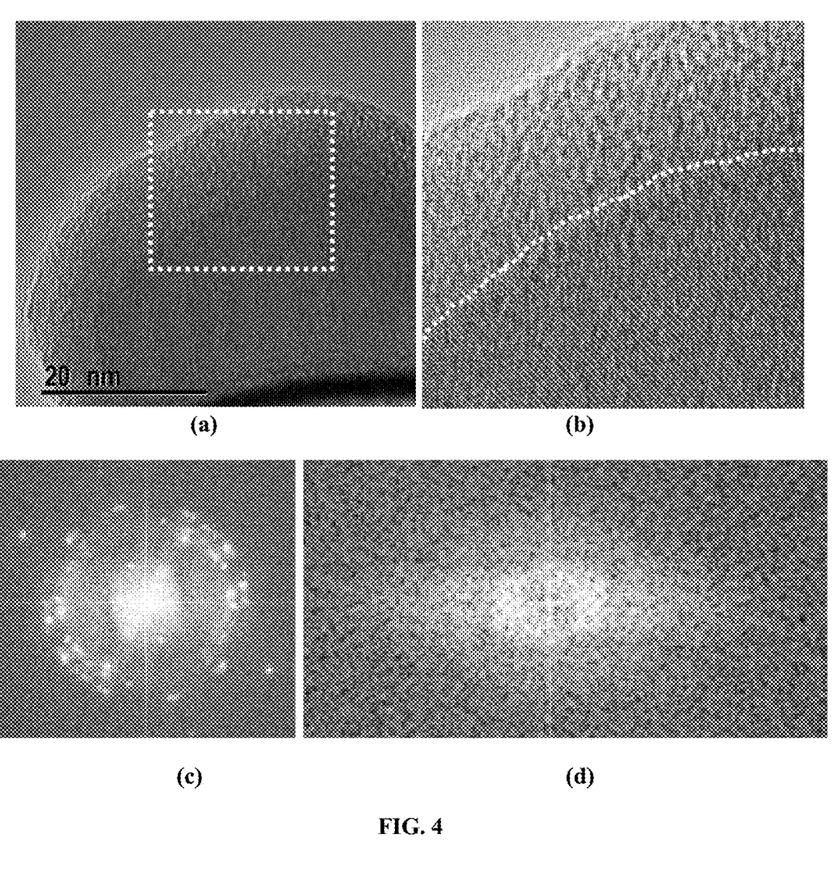
FIG. 4. Crystallinity degree analysis of calcium carbonate particles with 10% sodium caseinate: (a) Transmission electron microscopy 195000×; (b) Close-up on bounded zone in FIG. 4a, the dotted line indicates the boundary between protein (upper part) and calcium carbonate (lower part); (c) Diffraction patterns of the mineral on bounded zone in FIG. 4b; (d) Diffraction patterns of the protein coating on bounded zone in FIG. 4b.

The determination of the diffraction planes or crystallinity degree of the samples was carried out on a transmission electron microscope (Tecnai 12, FEI Electron Optics) equipped with an energy dispersive X-ray detector. Areas of the calcium carbonate samples with 2% protein (FIG. 3a, b) and 10% protein (FIG. 4a, b) were selected to determine the diffraction patterns of the mineral and protein. For the sample with 2% protein (FIG. 3c) and 10% protein (FIG. 4c) crystalline planes were detected for the calcium carbonate particles with interplanar distances of 1.650, 1.890, 2.490, 2.845 and 3.07 Å, corresponding to the mineral. For the sample with 2% protein, planes were detected in the protein zone with interplanar distances of 1.940 and 4.115 Å (FIG. 3d). These protein interplanar distances did not coincide with those detected for the mineral. Therefore, the adsorption process of the protein onto the mineral generated protein crystallization. This crystallization process was not observed for the system with 10% protein as no crystalline planes were detected in the protein zone (FIG. 4d).

Example 2. Production of Calcium Carbonate Coated with Protein and Polysaccharide (92% CaCO$_3$, 2% Protein, 6% Maltodextrin A solution of 200 g sodium caseinate (10% w/w) was prepared by hydration for at least 2 hours and cooling to 5° C. On the other hand, 1620 g of a calcium carbonate suspension (57% w/w) was prepared, which was then cooled to 5° C. and mixed with the sodium caseinate solution by stirring at 450 rpm. Once the mixing was completed, and while maintaining the agitation and a temperature below 8° C., 78 g of a calcium chloride dihydrate solution (5% w/w) was slowly added. This suspension was stirred for at least 1 h, keeping the temperature below 8° C., and then 600 g of a maltodextrin solution (10%) was added to obtain the suspension of calcium carbonate particles with protein coating and polysaccharides.

The suspension was dried in a spray dryer in co-current configuration at an inlet temperature of 310° C., outlet temperature of 90° C., ventilation rate of 150 m$^3$/h and feed pump speed of 60 mL/minute.

Figure 5:
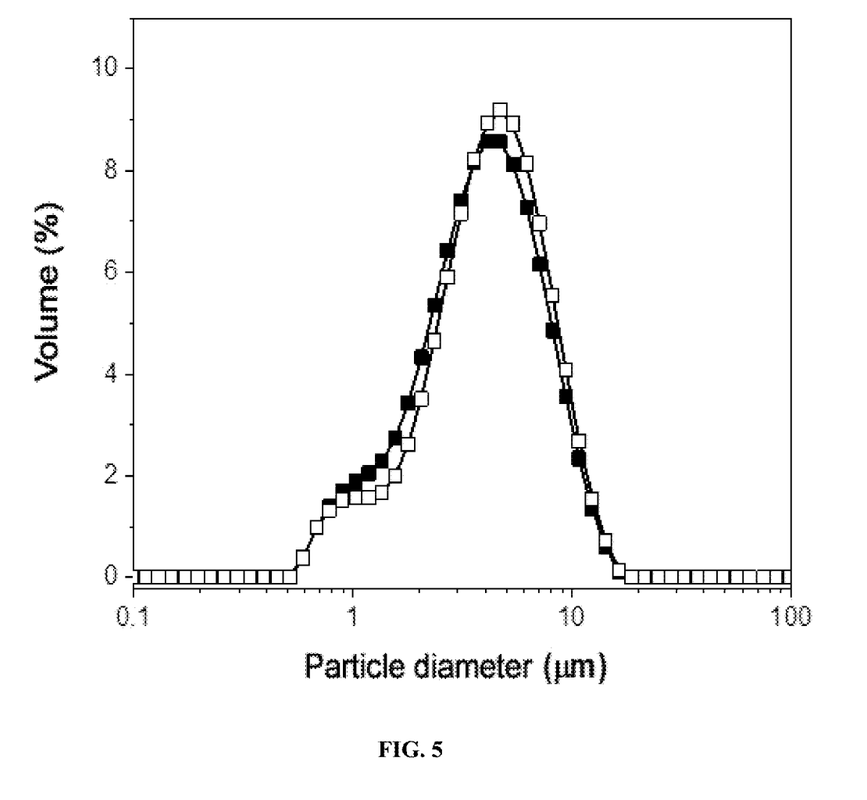
FIG. 5. Particle size distribution of calcium carbonate coated with protein and maltodextrin: ■, suspension before drying process; □, dried and redispersed particles in water (Example 2).

Measurement of particle size distribution (FIG. 5) was performed on a Mastersizer 2000 static light scattering instrument (Malvern Instruments, England). The calcium carbonate suspension coated with protein and polysaccharides presented a volume average size of 4.2 μm. After the spray drying process, the particles were aggregated increasing the average particle size to 53 μm. However, when the dried particles were redispersed in water, their disaggregation was achieved, obtaining a size distribution similar to the suspension before the drying process and with a volume average size of 4.5 μm. This demonstrated that the process of particle aggregation by the spray drying process is reversible. This aggregation-disaggregation property is required for applications in the food, cosmetic, nutraceutical and pharmaceutical industries, where the handling of dry powdered material with a particle size close to 50 μm is needed, which decreases inhalation hazards. However, once the powdered material is incorporated into an aqueous matrix, deagglomeration of the particles is required to avoid rapid settling.

Figure 6:
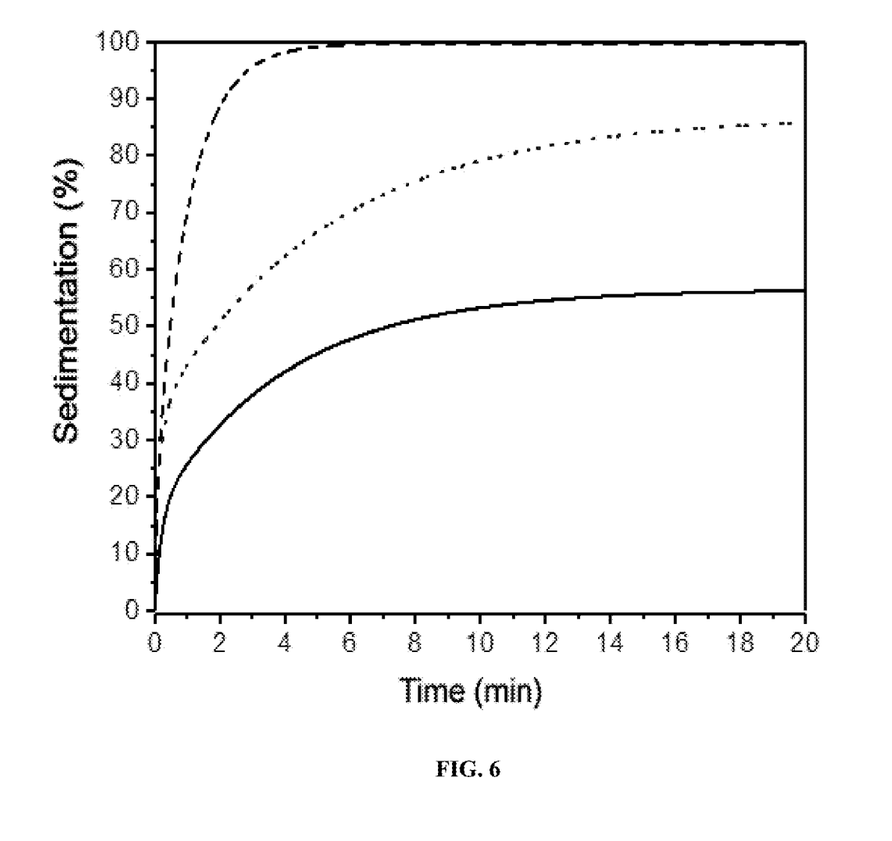
FIG. 6. Calcium carbonate particle sedimentation profiles: —98% $CaCO_3$ 2% Protein (2P); . . . 95% $CaCO_3$ 2% Protein 3% Maltodextrin (2P3M); —92% CaCO₃ 2% Protein 6% Maltodextrin (2P6M) (Example 2).

FIG. 6 presents the sedimentation profiles of the calcium carbonate coated with protein and polysaccharide (92% CaCO$_3$, 2% protein, 6% maltodextrin referred to herein as 2P6M) and an irreversibly added calcium carbonate (98% CaCO$_3$, 2% protein referred to herein as 2P) obtained according to the procedure of Example 1, with an average particle size of 22 μm. In this figure, it is evident that after 2 minutes the 2P6M system sedimented 30% of the particles mass, while the 2P system presented a sedimentation of 85% in the same time.

Example 3. Production of Calcium Carbonate Coated with Protein and Polysaccharide (95% CaCO$_3$, 2% Protein, 3% Maltodextrin A solution of 20 g sodium caseinate (10% w/w) was prepared by hydration for at least 2 hours and cooling to 5° C. On the other hand, 195 g of a calcium carbonate suspension (49% w/w) was prepared, which was then cooled to 5° C. and mixed with the sodium caseinate solution by stirring at 450 rpm. Once the mixing was completed, and while maintaining agitation and a temperature below 8° C., 100 g of a calcium chloride dihydrate solution (0.15% w/w) was slowly added. This suspension was stirred for at least 1 h, keeping the temperature below 8° C., and then 30 g of a maltodextrin solution (10%) was added to obtain the suspension of calcium carbonate particles with protein coating and polysaccharides.

The suspension was dried in a spray dryer in co-current configuration at an inlet temperature of 300° C., outlet temperature of 90° C., ventilation rate of 150 m$^3$/h and feed pump speed of 60 mL/minute.

FIG. 6 presents the sedimentation profile of calcium carbonate coated with protein and polysaccharide (95% CaCO$_3$, 2% protein, 3% maltodextrin named herein 2P3M), indicating that this system sedimented 50% of the particle mass after 2 min. Therefore, 2P3M calcium carbonate has a lower sedimentation tendency than the 2P system, but higher than the 2P6M system.

Example 4. Preparation of Ice Cream Mix with Calcium Carbonate Coated with Protein and Polysaccharides (95% CaCO$_3$, 2% Protein, 3% Maltodextrin The calcium carbonate coated with protein and polysaccharide of Example 3 (i.e., 2P3M) was incorporated at concentrations of 0.25% and 1.5% into an ice cream mix (8% milk powder, 5% whey, 8% vegetal fat, 15.7% sugar, 0.4% stabilizers).

The ice cream mixture was prepared by dispersing 412 g of whole milk powder and 267 g of whey in 3115 g of water at a temperature of 55° C. Subsequently, 402 g of hydrogenated palm fat was added and the temperature of the mixture was raised to 85° C. and maintained for 15 minutes. This mixture was homogenized in a high-pressure homogenizer at 3000 psi. The ice cream mixture obtained was refrigerated at 5° C. for 4 hours.

Figure 7:
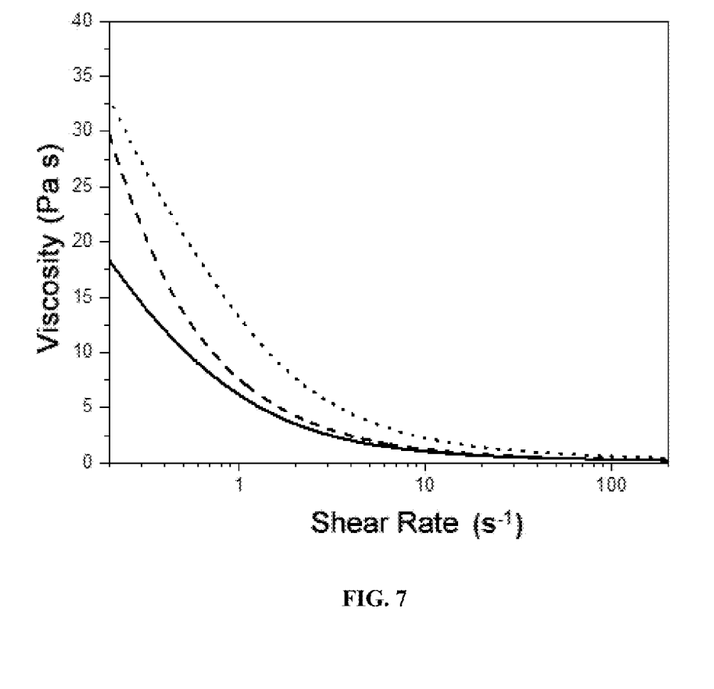
FIG. 7. Viscosity curve of ice cream mixture: —no calcium carbonate added; —0.25% w/w coated calcium carbonate (2P3M); . . . 1.50% coated calcium carbonate (2P3M) (Example 4).

The apparent viscosity of the refrigerated ice cream mixtures was measured in a shear rate range between 0.2 and 200 s$^{-1}$, using an HR Nano rheometer (Malvern Instruments, England) (FIG. 7). For a shear rate of 0.2 s$^{-1}$ the ice cream mixture viscosity without calcium addition was of 18 Pa s, which increased to 30 Pa s and 33 Pa s for the ice cream mixtures with addition of calcium carbonate coated with protein and maltodextrin at concentrations of 0.25 and 1.5%, respectively. This significant increase in viscosity of the ice cream mixes with calcium addition did not affect the ice cream aeration process, on the contrary, it decreased the aeration time by 25%. Additionally, the addition of calcium carbonate coated with protein and maltodextrin allowed to control the melting of the ice cream as a finished product. The melting test was performed at 20° C. and taking an ice cream ball of mass close to 35 g supported on a stainless-steel mesh with 20 holes per square inch. The melted mass was collected in a container placed on a balance that allowed tracking the mass of melted ice cream for a period of up to 110 minutes.

Figure 8:
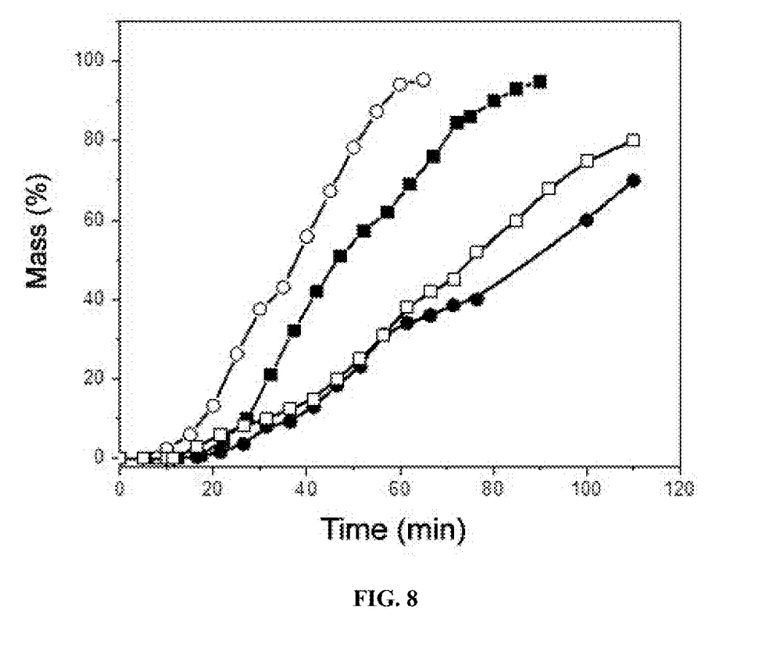
FIG. 8. Melting profile of ice cream: ■, 0% CaCO₃ and vegetal fat; □, 0% CaCO₃ and milk fat; ●, 0.25% CaCO₃ coated with protein and polysaccharide (2P3M) and vegetal fat; ○, 1.50% CaCO₃ coated with protein and polysaccharide (2P3M) and vegetal fat (Example 4).

FIG. 8 shows the melting curves of ice cream made with vegetal fat and cow's milk fat without addition of calcium carbonate and ice cream made with vegetal fat and addition of 2P3M calcium carbonate at concentrations of 0.25% and 1.5%. The melting profile of the cow's milk fat ice cream showed 35% melted mass after 60 minutes, while the vegetal fat ice cream showed 70% melted mass. The addition of 2P3M calcium carbonate at a concentration of 1.5% generated a melting profile similar to that observed for the vegetal fat ice cream. However, the addition of 0.25% 2P3M calcium carbonate produced a melting profile similar to that obtained for the cow's milk fat ice cream, with 34% melted mass after 60 minutes.

Example 5. Production of Calcium Carbonate Tablets Coated with Protein and Polysaccharides (95% $CaCO_3$, 2% Protein, 3% Maltodextrin Calcium carbonate coated with protein and polysaccharide of Example 3 (i.e., 2P3M) was employed for the preparation of calcium carbonate tablets and tested for its dissolution property in acidic medium.

Tablets were processed on a Rimek® 36-station rotary tablet press. The tableting pressure was set at 25 MPa and a tablet weight of 1390 mg with a processing speed of 500 tablets/minute. The tablets obtained by direct compression had a hardness of 15 kPa.

The dissolution test was carried out in a DT8 Dissolver (Erweka GmbH, USA) at a temperature of 37° C. and a stirring of 75 rpm. The acidic medium used was a 0.1 M HCl solution.

The dissolution test showed that the calcium carbonate tablet (98% 2P3M, 2% Polyplasdone) showed 84% dissolution in a time of 30 minutes, indicating its feasibility of use as a direct compression active ingredient for nutraceutical and pharmaceutical products.

Example 6. Processing of Protein-Coated Kaolin (96% Kaolin, 4% Protein

A 2000 g suspension of kaolin (5% w/w) was prepared, to which 4.2 g of sodium caseinate was added by continuous stirring at 500 rpm. This suspension was kept in agitation for at least 8 hours, and then the system was cooled down to a temperature below 8° C. Subsequently, 6 g of a calcium chloride dihydrate solution (5% w/w) was slowly added to obtain the suspension of protein-coated kaolin particles.

The protein-coated kaolin suspension was subsequently dried in a spray dryer in disc configuration at an inlet temperature of 320° C., outlet temperature of 90° C., ventilation rate of 150 m$^3$/h and feed pump speed of 50 mL/minute.

Figure 9:
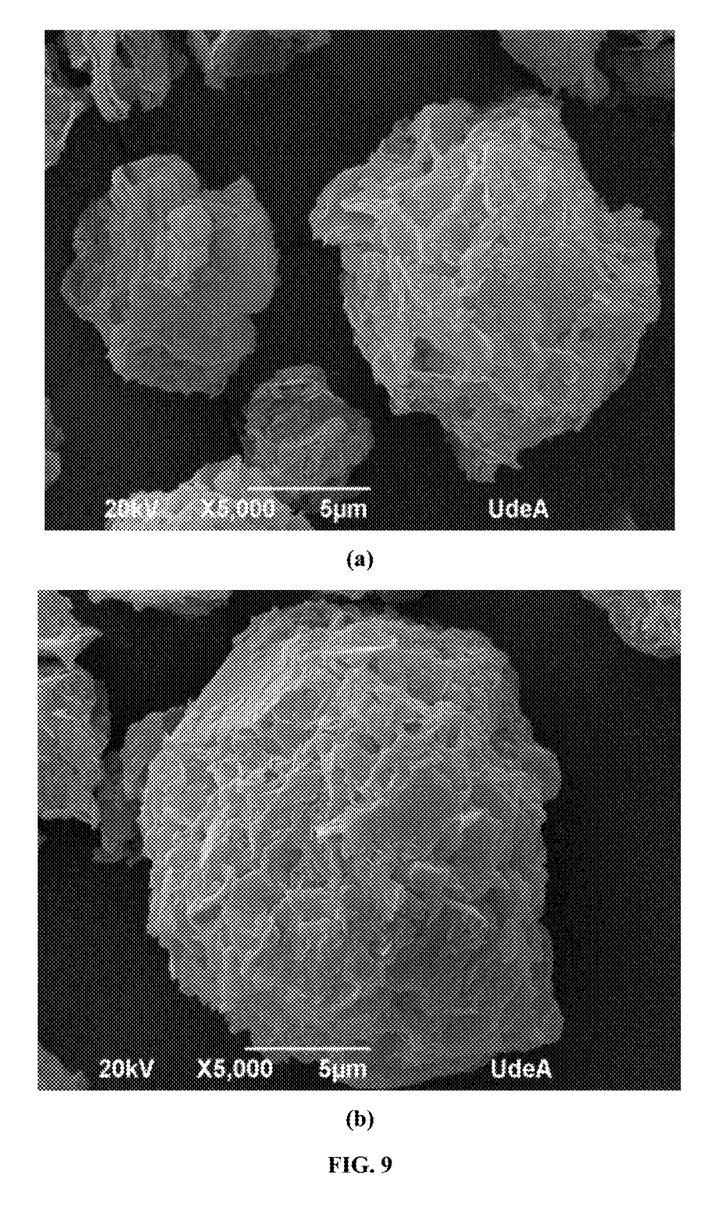
FIG. 9. Scanning electron micrographs of kaolin with sodium caseinate: (a) 2% protein; (b) 10% protein (Example 6).

The contact angle measurement of the mineral coated with 4% protein, using the Washburn method in an automatic tensiometer K-12 (Krüss) generated a value close to 75°. Meanwhile, kaolin microcapsules with a protein content equal to or higher than 10% presented contact angles close to 90°. The scanning electron micrographs (FIG. 9A and FIG. 9B) present a comparison of the 4% and 10% protein coated particles. For the 4% system, agglomerates of particles with a size close to 10 µm and an amorphous morphology generated by the kaolin sheets, bound by the protein, were observed. For the system with 10% protein, the particle agglomerates were close to 15 µm in size and presented a spheroidal morphology with a compact and organized surface of the kaolin sheets.

The free protein measurement by ultraviolet-visible spectrophotometry, indicated a value lower than 5% for the system 96% Kaolin and 4% protein, while the values obtained for the system 90% Kaolin and 10% protein, presented free protein values between 10 and 20%.

Example 7. Production of Kaolin Coated with Protein (96% Tricalcium Phosphate, 4% Protein A solution of 35.7 g sodium caseinate (10% w/w) was prepared by hydration for at least 2 hours and cooling to 5° C. On the other hand, 630 g of a tricalcium phosphate suspension (15% w/w) was prepared, which was then cooled to 5° C. and mixed with the sodium caseinate solution by stirring at 450 rpm. Once the mixing was finished, and keeping the temperature below 8° C., 5.5 g of a calcium chloride dihydrate solution (5% w/w) was slowly added to obtain the suspension of tricalcium phosphate particles with protein coating.

The protein-coated tricalcium phosphate suspension was subsequently dried in a spray dryer, in a disc configuration, at an inlet temperature of 300° C., outlet temperature of 90° C., ventilation rate of 160 m$^3$/h and feed pump speed of 60 mL/minute.

Figure 10:
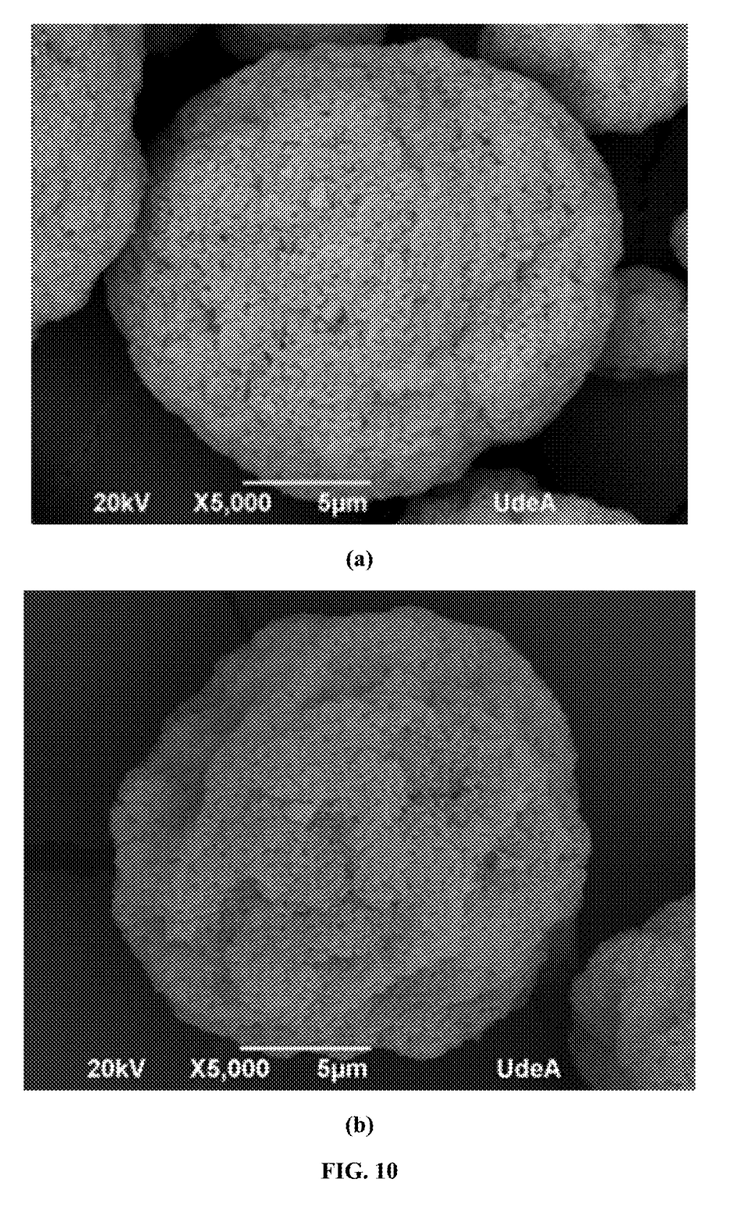
FIG. 10. Scanning electron micrograph of tricalcium phosphate with sodium caseinate: (a) 4% protein; (b) 10% protein (Example 7).

The contact angle measurement of the mineral coated with 4% protein, using the Washburn method in an automatic tensiometer K-12 (Krüss) generated a value close to 63°. Meanwhile, tricalcium phosphate microcapsules with a protein content equal to or higher than 10% presented contact angles close to 90°. The scanning electron micrographs (FIG. 10A and FIG. 10B) present a comparison of the particles coated with 4% and 10% protein. For both systems, the particle size was similar and close to 15 µm, however, the system with 4% protein showed a spheroidal surface of higher roughness than the system with 10% protein.

Example 8. Production of Protein-Coated Calcium Carbonate (94% $CaCO_3$, 6% Protein A solution of 200 g sodium caseinate (10% w/w) was prepared by hydration for at least 2 hours and cooling to 5° C. On the other hand, 700 g of a calcium carbonate suspension (45% w/w) was prepared, which was then cooled to 5° C. and mixed with the sodium caseinate solution by stirring at 450 rpm. Once the mixing was finished, and keeping the temperature below 8° C., 100 g of a calcium chloride dihydrate solution (0.51% w/w) was slowly added to obtain the suspension of calcium carbonate particles with protein coating.

The protein-coated calcium carbonate suspension was subsequently dried in a spray dryer in disc configuration at an inlet temperature of 320° C., outlet temperature of 90° C., ventilation rate of 150 m3/h and feed pump speed of 50 mL/minute.

Figure 11:
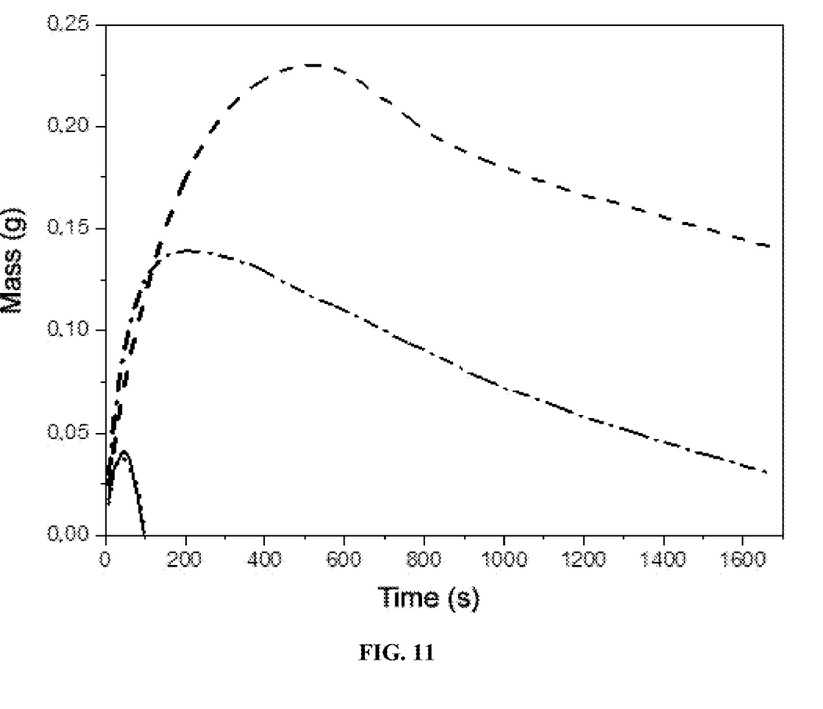
FIG. 11. Decomposition profile of calcium carbonate tablets with sodium caseinate: —0% protein; . . . 2% protein; . . . 6% protein; —10% protein (Example 8).

The acid decomposition profile of a calcium carbonate tablet was performed using an automatic tensiometer K-12 (Krüss) by placing it in contact with a 0.1 M hydrochloric acid solution. The tensiometer recorded the mass of the calcium carbonate tablets as a function of time (FIG. 11). Initially, the tablets showed a mass gain due to hydration of the tablets to a maximum value, and then showed mass loss as the calcium carbonate tablet began the decomposition process of the calcium carbonate tablet into carbon dioxide. For the calcium carbonate tablets without protein and with 2% protein, the beginning of the decomposition process was observed after 50 s. Therefore, coating the mineral with 2% protein did not provide protection against acid decomposition. On the other hand, tablets with 6% and 10% protein showed decomposition after 200 and 500 s, respectively. This indicates that a protein concentration equal to or higher than 10% protein is required to achieve high stability to acid decomposition of calcium carbonate.

The invention claimed is:
1. A process for coating water-insoluble solids by ionic gelation, comprising:
  a) preparing an aqueous suspension of water-insoluble solids between 1% and 80% (w/w) and an aqueous solution of negatively charged macromolecules between 0.1% and 40% w/w wherein the negatively charged macromolecules are selected from proteins, polysaccharides and mixtures thereof;

b) mixing the aqueous macromolecule solution with the aqueous suspension of insoluble solids in water with agitation between 200 rpm and 500 rpm and at a temperature between 2° C. and 8° C.;

c) adding a calcium salt at a concentration between 0.1% and 10% (w/w), to the mixture of step (b) until a film is formed to cover the insoluble solid, and raising the temperature up to 25° C.;

d) drying the particles obtained from step c) by spray-drying at temperatures between 80° C. and 400° C.;

wherein the water-insoluble solids are selected from metallic and non-metallic minerals, phyllosilicates, polymeric particles, kaolin, calcium salts, calcium oxides or mixtures thereof;

wherein the calcium salt of step c) is selected from calcium chloride, calcium chloride dihydrate, calcium oxalate and calcium citrate;

wherein the negatively charged macromolecules content is less than 10% (w/w) of the total weight of the coated solid;

wherein the coating film thickness of the water-insoluble solids obtained is less than 10 nm;

wherein the coated particles have a contact angle between 20° and 89° determined by the Washburn method; and wherein the particles obtained from step d) have a moisture content lower than 5%.

2. The process according to claim 1, wherein the water-insoluble solids are selected from iron oxides, magnesium oxides, zinc oxides, calcium carbonates, calcium sulfates, calcium phosphates, aluminosilicates, kaolin or mixtures thereof.

3. The process according to claim 2, wherein the water-insoluble solids are selected from aluminosilicates, calcium carbonate, calcium phosphate, calcium sulfate, or mixtures thereof.

4. The process according to claim 1, wherein the negatively-charged macromolecules are selected from milk proteins, protein salts, gelatin, proteins from vegetal sources, albumins, or mixtures thereof.

5. The process according to claim 4, wherein the negatively-charged macromolecules are selected from casein, sodium caseinate, calcium caseinate, whey proteins, pea, soy, gum arabic, xanthan, alginate salts, cellulose derivatives, modified starches, pectin salts, carrageenans, polyacrylates, polysulphates and polysulphonates or mixtures thereof.

6. The process according to claim 1, wherein the calcium salt is at a concentration between 0.2 M and 2 M.

7. The process according to claim 1, wherein additionally a step (e) takes place, wherein a neutral, cationic and/or reducing sugar type polysaccharide is added after adding the calcium salt to the aqueous macromolecule solution, with the aqueous suspension of water-insoluble solids, wherein the neutral, cationic and/or reducing sugar type polysaccharide is selected from guar gum, agar, maltodextrins, cyclodextrins and chitosan.

8. A water-insoluble solid coated by a coating film of negatively charged macromolecules obtained from the process of claims 1, wherein:

the water-insoluble solids are selected from metallic and non-metallic minerals, phyllosilicates, polymeric particles, kaolin, calcium salts, calcium oxides or mixtures thereof;

the negatively charged macromolecules are selected from proteins, polysaccharides and mixtures thereof;

the content of macromolecules in the coating is less than 10% (w/w) of the total weight of the coated solid;

the coating film thickness of the water-insoluble solids obtained is less than 10 nm;

wherein the coated particles have a contact angle between 20° and 89° determined by the Washburn method; and wherein the spray-dried particles have a moisture content lower than 5%.

* * * * *